(12) United States Patent
Karlsson

(10) Patent No.: US 9,579,467 B2
(45) Date of Patent: Feb. 28, 2017

(54) SAFETY PEN NEEDLE DEVICE

(71) Applicant: SHL Group AB, Nacka Strand (SE)

(72) Inventor: Sebastian Karlsson, Sundbyberg (SE)

(73) Assignee: SHL Group AB, Nacka Strand (SE)

( * ) Notice: Subject to any disclaimer, the term of this patent is extended or adjusted under 35 U.S.C. 154(b) by 37 days.

(21) Appl. No.: 14/300,344

(22) Filed: Jun. 10, 2014

(65) Prior Publication Data

US 2015/0032058 A1  Jan. 29, 2015

Related U.S. Application Data

(63) Continuation of application No. 13/266,253, filed as application No. PCT/SE2010/050450 on Apr. 23, 2010, now Pat. No. 8,858,510.

(30) Foreign Application Priority Data

Apr. 27, 2009  (SE) ...................... 0950278

(51) Int. Cl.
*A61M 5/32* (2006.01)
*A61M 5/50* (2006.01)
*A61M 25/06* (2006.01)

(52) U.S. Cl.
CPC ........ *A61M 5/3245* (2013.01); *A61M 5/3272* (2013.01); *A61M 5/5086* (2013.01); *A61M 5/326* (2013.01); *A61M 5/3271* (2013.01); *A61M 25/0612* (2013.01); *A61M 25/0631* (2013.01); *A61M 2005/3267* (2013.01)

(58) Field of Classification Search
CPC .............. A61M 5/3245; A61M 5/3232; A61M 5/3234; A61M 5/3272; A61M 5/3271; A61M 5/3243; A61M 5/5086; A61M 5/50; A61M 5/326; A61M 2005/3254;

(Continued)

(56) References Cited

U.S. PATENT DOCUMENTS 5,242,401 A * 9/1993 Colsky .................. A61M 5/326
604/110
6,428,517 B1 * 8/2002 Hochman ............... A61M 5/00
604/151

(Continued)

FOREIGN PATENT DOCUMENTS

WO  01/76665 A1  10/2001

*Primary Examiner* — Imani Hayman
*Assistant Examiner* — Nilay Shah
(74) *Attorney, Agent, or Firm* — McDonnell Boehnen Hulbert & Berghoff LLP

(57) ABSTRACT

A safety needle device comprising a needle hub, an attachment mechanism arranged at the distal end for attaching the safety needle device to a medicament container, and a coaxially arranged needle attachment member. The safety needle device also comprises an injection needle comprising a proximal pointed injection end and a distal pointed non-injection end arranged to penetrate a septum of a medicament container, the injection needle being attached inside the needle hub and extending through the needle attachment member. A rotator arranged to rotate on the hub, the rotator arranged with an annular wall provided with a central passage, such that the needle attachment member of the needle hub extends through a central passage of the rotator. A needle shield surrounds the rotator and slidably arranged with respect to the hub and the rotator.

19 Claims, 12 Drawing Sheets

(58) Field of Classification Search
CPC .......... A61M 25/0612; A61M 25/0631; A61M 2039/042; A61M 5/3293
See application file for complete search history.

(56) References Cited

U.S. PATENT DOCUMENTS

| | | | |
|---|---|---|---|
| 6,547,764 B2* | 4/2003 | Larsen | A61M 5/326 |
| | | | 604/110 |
| 6,702,784 B1 | 3/2004 | Sheckler et al. | |
| 7,001,364 B1* | 2/2006 | Farhi | A61M 5/3272 |
| | | | 604/110 |
| 2005/0065476 A1* | 3/2005 | Jensen | A61M 5/326 |
| | | | 604/197 |
| 2008/0077093 A1* | 3/2008 | Gratwohl | A61M 5/3257 |
| | | | 604/198 |

* cited by examiner

SAFETY PEN NEEDLE DEVICE

CROSS REFERENCE TO RELATED APPLICATIONS

The present application is a continuation application of U.S. patent application Ser. No. 13/266,253 filed Oct. 26, 2011, issued as U.S. Pat. No. 8,858,510, which is a 35 U.S.C. 371 National Application of PCT/SE2010/050450 filed Apr. 23, 2010, which claims priority to Swedish Patent Application No. 0950278-2 filed Apr. 27, 2009 the entire contents of which are incorporated entirely herein by reference.

TECHNICAL AREA

The present invention relates to a safety pen needle device to be used with a medicament delivery device and in particular a safety pen needle device providing added security against accidental needle sticks.

TECHNICAL BACKGROUND

Accidental needle sticks from used and thereby contaminated needles expose both hospital personnel and other persons that come in contact with people that self-medicate to the risk of infection from blood-borne diseases.

Even though the majority of injection devices used is the normal syringe the use of pen needle injectors is becoming more and more popular since they provide the possibility of an easy and convenient self-administration of drugs. The pen-type injectors are also becoming the only choice for certain types of drugs because they are not delivered in ordinary single use syringes.

In order to reduce the risk of accidental needle sticks, many pen injectors have been arranged with needle shields that are capable of covering said needle after injection. These needle shields may be useful but they add to the complexity and number of components of the injector. Further, if the injector is designed to deliver multiple doses, then the needle has to be replaced after each injection. This adds to the risk of accidental needle sticks and if the injector is arranged with a needle cover, this will be in the way when the needle is to be replaced.

Injections where a liquid is expelled into the human body are usually performed either as intramuscular injections i.e. injections into the muscle tissue, or as subcutaneously injections i.e. injections into the subcutaneous tissue lying between the cutis and the muscle tissue. When performing intramuscular injections, long injections needles are used. The outside diameters of injection needles are indicated by a "G" and a gauge number increases with thinner needles. Thus the outside diameter of a G 23 is 0.60 mm and of a G 2 0.50 mm. Long injection needle has a diameter of 23 G for a 25 mm long injection needle and 25 G for a 16 mm long injection needle. It has for some years been known to provide long injection needles with safety protective devices in order to prevent accidental needle stick injuries. Such safety protective devices are e.g. known from EP 409 180 and U.S. Pat. No. 4,813,940. These known safety protective devices comprises a number of telescopic sleeves, which telescopic sleeves slides into each other in order to expose an injection needle covered by the telescopic sleeves when not in use. However, some medicines have to be injected subcutaneously i.e. in the subcutis lying between the cutis and a muscle membrane which cover the underlying muscles. When performing subcutaneous injections, short and thin injections needles are used and these short needles have also safety protective devices, wherein the combination of the short needle and the safety protective device is known as a safety pen needle.

A few safety pen needle solutions have been developed in order to minimize the risk of accidental needle sticks.

One such solution is disclosed in the U.S. Pat. No. 7,462,168. Therein is described a safety pen needle with a passive safety shield system. It comprises a central hub to which an injection needle is attached, where the needle is provided with an injection end and a non-injection end, and where the latter is intended to penetrate a septum of a medicament container when mounted. Outside the hub a sleeve is slidably arranged and further a shield is slidably arranged to the sleeve in a kind of telescopic manner. The sleeve and the shield are both urged in the proximal direction by a compression spring. When the injection is performed the shield is pushed into the sleeve, which in turn slides in relation to the hub, thereby exposing the injection end of the needle. When the shield is fully depressed in relation to the sleeve, it becomes locked to the sleeve and they move in tandem during continued penetration. When the device is removed after injection, the sleeve and shield are moved in the proximal direction by the compression spring until tabs on the sleeve enter lock out recesses on the hub such that the sleeve and thus the shield are locked and the needle is protected. Further the safety pen needle according to U.S. Pat. No. 7,462,168 comprises a safety system for the non-injection end of the needle. It comprises a non-injection end shield slidable in relation to the hub. A protrusion on the hub cooperates with tracks on the shield to first allow the shield to be pushed into the hub when mounted on a medicament container and then to lock said shield in an extended position when removed from the container, where the tracks have a first straight part and a latter inclined part with a depression for locking the shield. However, probably functioning correctly in covering the needle, the safety pen needle according to '168 comprises a lot of interacting components in order to obtain the desired function, which makes the design rather difficult to manufacture and thereby rather costly.

Another solution is found in EP1289587B1 which discloses a disposable double pointed safety pen needle having a needle hub to which a thin needle cannula is permanently fastened and which needle hub can be mounted onto a syringe comprising a dose setting and injection mechanism and a cartridge containing a liquid medicine to be injected subcutaneously into a human body. The needle hub is provided with a safety shield guided on the outside surface of the needle hub. The safety shield is urged in a direction away from the needle hub by a spring located between the needle hub and the safety shield. The safety shield has a number of protrusions guided in guiding tracks on the outside surface of the needle hub. The guiding tracks are designed such that the safety shield during injection is displaced towards the needle hub by a translation movement and after injection is longitudinally moved away from the needle hub by the spring and locked in an irreversible position where the safety shield covers the needle cannula and prevents accidental needle stick injuries. Since the shield is in contact with an injection site and the shield is moved by a translation movement, i.e. a rotationally longitudinal displacement, the contact between the shield and the injection site i.e. the skin of a patient, is affected by a friction which may result in an ineffective function of the safety pen needle.

A further solution is known from US 2005 065 476 A1 which discloses a safety needle assembly comprising a cylindrical housing adapted to be attached to a medical injection device, a needle cannula attached to the housing, a shield telescopically movable relatively to the housing for movement between a distal position where the shield covers the distal end of the needle cannula and a proximal position where at least a part of the distal end of the needle cannula is exposed, a spring located inside said housing urging the shield in the distal direction, and a locking element longitudinal having locking protrusions and being moved simultaneously with the shield relatively to the housing during use. However, US 2005 065 476 A1 also discloses that since the locking element is provided as a separate element located between the spring and the shield and moved simultaneously with the shield, the locking protrusion can be guided during the longitudinal movement of the locking element thereby eliminating the need for tracks or cams.

BRIEF DESCRIPTION OF THE INVENTION

A main aim of the present invention is to remedy the drawbacks of the safety pen needle devices of the state of the art and in particular to provide a safety pen needle device capable of performing a proper function with few components.

This aim is obtained by the features of the independent patent claim. Preferable embodiments of the invention form the subject of the dependent patent claims.

According to a major aspect of the invention, it is characterised by a safety pen needle device comprising a generally tubular hub having a proximal and a distal end, said hub comprising attachment means arranged at its distal end for attaching the safety pen needle device to a medicament container assembly, and a coaxially arranged needle attachment member; an injection needle having an injection end and a non injection end, said injection needle being attached inside said hub and extending through the needle attachment member; wherein said device further comprises a generally tubular rotatable sleeve rotatable arranged on said hub, said rotatable sleeve comprising on its outer circumferential surface at least one guide track comprising flexible means; a generally tubular needle shield slidably arranged on said rotatable sleeve, said needle shield comprising at least one guide protrusion on its inner circumferential surface, wherein said at least one protrusion is arranged to interact with said at least one guide track and with said flexible means; and resilient means co-acting with said needle shield for urging said needle towards the distal end of the device.

According to another aspect of the invention, the at least one guide track comprise at least one inclined section, such that when the needle shield is linearly displaced on the rotatable sleeve and said at least one guide protrusion pass through the at least one inclined section, the rotatable sleeve is forced to rotate on the hub.

According to yet another aspect of the invention, wherein said needle shield is arranged with an end wall, which end wall is provided with a central opening through which injection end of the injection needle may pass.

According to a further aspect of the invention, said needle shield is arranged to be linearly displaced on the rotatable sleeve from an initial position in which said needle shield is surrounding the injection end of said injection needle to an injection position in which the injection end of said injection needle is exposed outside said needle shield after said needle shield has been displaced towards the distal end of the device by having pressed said needle shield against an injection site.

According to another aspect of the invention, the flexible means comprises a first flexible tongue.

According to yet another aspect of the invention, a recess is arranged between the boundaries of the at least one guide track and the boundaries of the first flexible tongues, and wherein said recess in arranged to co-act with said at least one protrusion for locking said needle shield to the rotator when the needle shield is displaced from the injection position to the initial position.

According to yet a further aspect of the invention, the inclined section is designed in such a form that when the needle shield is displaced from the initial position to the injection position, the rotatable sleeve is forced to rotate on the hub.

According to another aspect of the invention, the resilient means is arranged between an annular wall of the rotatable sleeve and the inner surface of the end wall of the needle shield.

According to yet another aspect of the invention, the resilient means is arranged between an annular wall of the hub and the inner surface of the end wall of the needle shield.

According to a further aspect of the invention, the resilient means are arranged to be compressed for accumulating a force when the needle shield is displaced from the initial position to the injection position, such that when the device is removed from the injection site, the needle shield is displaced from the injection position to the initial position by the force of the resilient member.

According to yet a further aspect of the invention, the inclined section is designed in such a form that when the needle shield is displaced from the injection position to the initial position, the rotatable sleeve is forced to rotate on the hub.

According to another aspect of the invention, needle shield comprises windows and said rotatable sleeve comprises audible and/or visual and/or tactile indicia arranged to interact with said windows for giving an indication that said device has been used.

There are a number of advantages with the present invention. Because of guide protrusions co-acting with guide tracks, wherein a rotator is positioned between the hub and the needle shield, guiding the needle shield to the final position, a safe and reliable locking of the needle shield is obtained with very few components, without the risk of turning/rotation problems of the needle shield when contacting the injection site i.e. the tissue/skin of a patient, because the turning/rotation is performed by the tubular rotatable sleeve positioned between the hub and the needle shield.

Further, since the needle shield is the outermost component, a rather large contact surface is obtained when the safety pen needle device is pressed against an injection site i.e. the tissue/skin of a patient, more pleasant feeling for the patient.

Further, the guiding of the needle shield, performed by turning the tubular rotatable sleeve from one position to another, is the key to obtain the desired function by so few components.

There is thus provided a reliable and functional safety pen needle comprising a small number of components, thereby keeping the production costs at low levels.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

Figure 1:
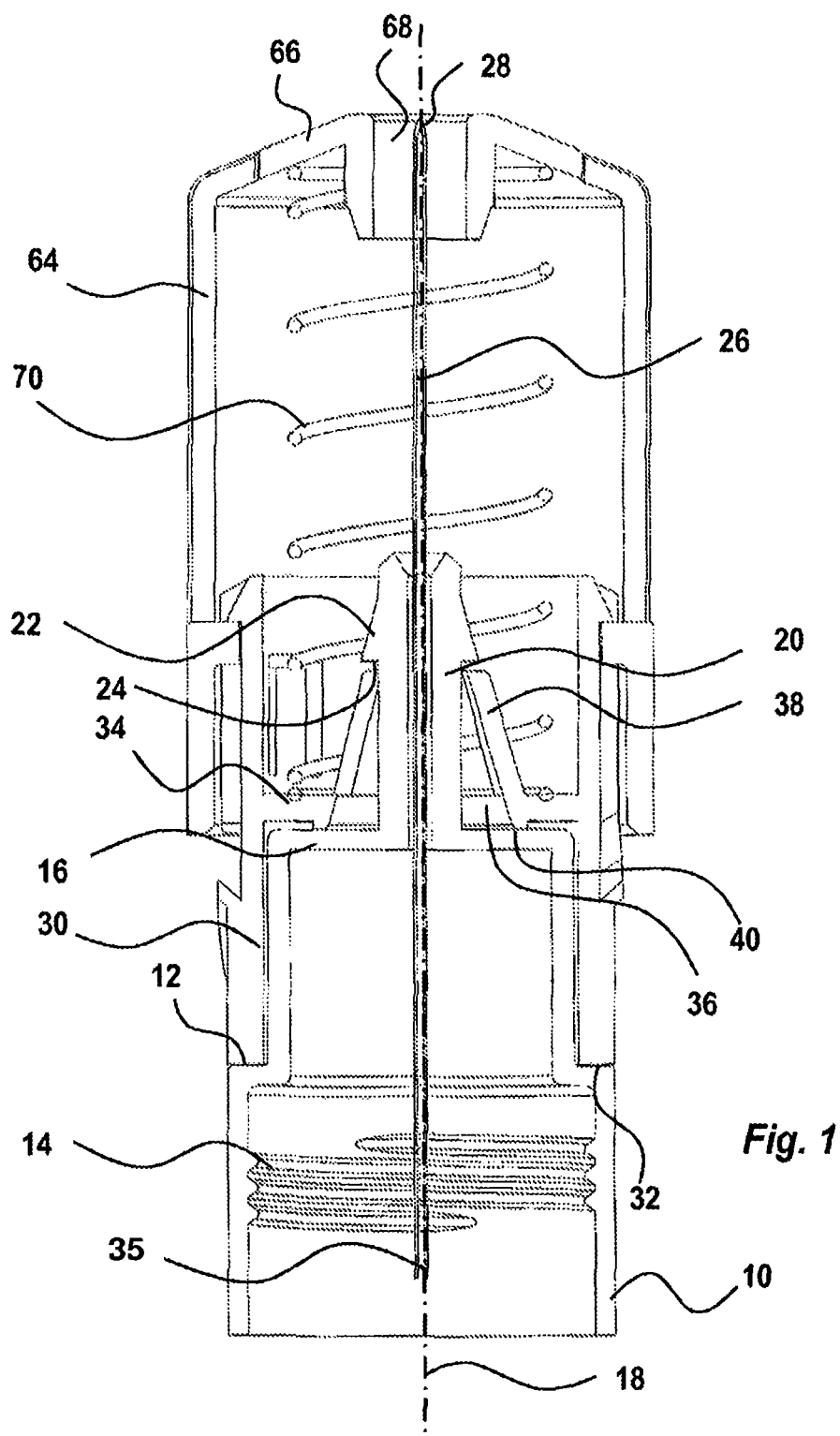
FIG. 1 shows a cross-sectional side view of a safety pen needle device according to the present invention in an initial position.

In the present application, when the term "distal part/end" is used, this refers to the part/end of the device, or the parts/ends of the members thereof, which during use of the device is located the furthest away from an injection site. Correspondingly, when the term "proximal part/end" is used, this refers to the part/end of the device, or the parts/ends of the members thereof, which during use of the device is located closest to the injection site.

The wording safety pen needle device is defined as the combination of a short and thin needle used for subcutaneous injections and safety protective means. The wording short and thin needle is defined as a needle having a diameter thinner than G 29 and a length in the interval of 6 to 12 mm.

According to a major aspect of the invention, it is characterised by a safety pen needle device comprising:

a generally tubular hub 10; 80 having a proximal and a distal end, said hub comprising attachment means 14; 82 arranged at its distal end for attaching the safety pen needle device to a medicament container assembly, and a coaxially arranged needle attachment member 20; 88;

an injection needle 26; 90 having an injection end 28; 92 and a non injection end 35; 94, said injection needle being attached inside said hub and extending through the needle attachment member;

a generally tubular rotatable sleeve 30; 91 rotatable arranged on said hub, said rotatable sleeve comprising on its outer circumferential surface at least one guide track 46; 98 comprising flexible means 58; 100,108;

a generally tubular needle shield 64; 112 slidably arranged on said rotatable sleeve, said needle shield comprising at least one guide protrusion 74, 120 on its inner circumferential surface, wherein said at least one protrusion is arranged to interact with said at least one guide track 46; 98 for guiding a linear movement of the needle shield in relation to the rotatable sleeve and for forcing the rotatable sleeve to rotate in relation to the hub, and wherein said at least one protrusion is also arranged to interact with said with said flexible means either for locking said needle shield to the rotatable sleeve when the device has been used or for guiding the linear movement of the needle shield in relation to the rotatable sleeve and for forcing the rotatable sleeve to rotate in relation to the hub and for locking said needle shield to the rotatable sleeve when the device has been used; and resilient means 70; 116 co-acting with said needle shield for urging said needle towards the distal end of the device.

According to another aspect of the invention, the at least one guide track 46; 98 comprise at least one inclined section 50; 103, such that when the needle shield is linearly displaced on the rotatable sleeve and said at least one guide protrusion 74, 120 pass through the at least one inclined section 50; 103, the rotatable sleeve is forced to rotate on the hub 10; 80.

According to yet another aspect of the invention, the needle shield is arranged with an end wall 66; 114, which end wall is provided with a central opening 68; 117 through which injection end of the injection needle may pass, and the needle shield 64; 112 is arranged to be linearly displaced on the rotatable sleeve from an initial position in which said needle shield is surrounding the injection end of said injection needle to an injection position in which the injection end of said injection needle is exposed outside said needle shield after said needle shield has been displaced towards the distal end of the device by having pressed said needle shield against an injection site.

According to a further aspect of the invention, the resilient means 70; 116 are arranged to be compressed for accumulating a force when the needle shield is displaced from the initial position to the injection position, such that when the device is removed from the injection site, the needle shield is displaced from the injection position to the initial position by the force of the resilient member.

According to yet a further aspect of the invention, the flexible means comprises a first flexible tongue 58; 108.

According to another aspect of the invention, a recess 62; 104) is arranged between the boundaries of the at least one guide track 46; 98 and the boundaries of the first flexible tongues 58; 108, and wherein said recess in arranged to co-act with said at least one protrusion 74; 120 for locking said needle shield to the rotator when the needle shield is displaced from the injection position to the initial position.

An exemplary first embodiment of the present invention is shown in the FIGS. 1-6. In FIG. 1 is shown the generally tubular hub 10 having the proximal and the distal end. The hub comprises two different diameters, thereby forming a circumferential ledge 12 facing the proximal direction. An inner circumferential surface of the hub at the distal end thereof is arranged with attachment means such as threads 14, which are arranged to cooperate with corresponding attachment means such as threads of a medicament container assembly (not shown) i.e. a medicament container or a container holder. An end wall 16 is arranged in the proximal end of said hub extending generally transversal in relation to a longitudinal direction 18 of the device. The needle attachment member 20 is arranged to, or made integral with, said end wall 16, where the needle attachment member has a generally cylindrical shape apart from an area around the proximal end of the needle attachment member, which has a conical shape 22, thereby forming an annular surface 24 facing the distal direction. In the centre of the needle attachment member the hollow injection needle 26 is attached. The injection needle 26 is provided with the proximal pointed injection end 28 and the distal pointed non-injection end 35, where the latter is arranged to penetrate a septum of the medicament container in order to provide a passage from the container through the needle 26 to the proximal injection end 28.

Figure 2:
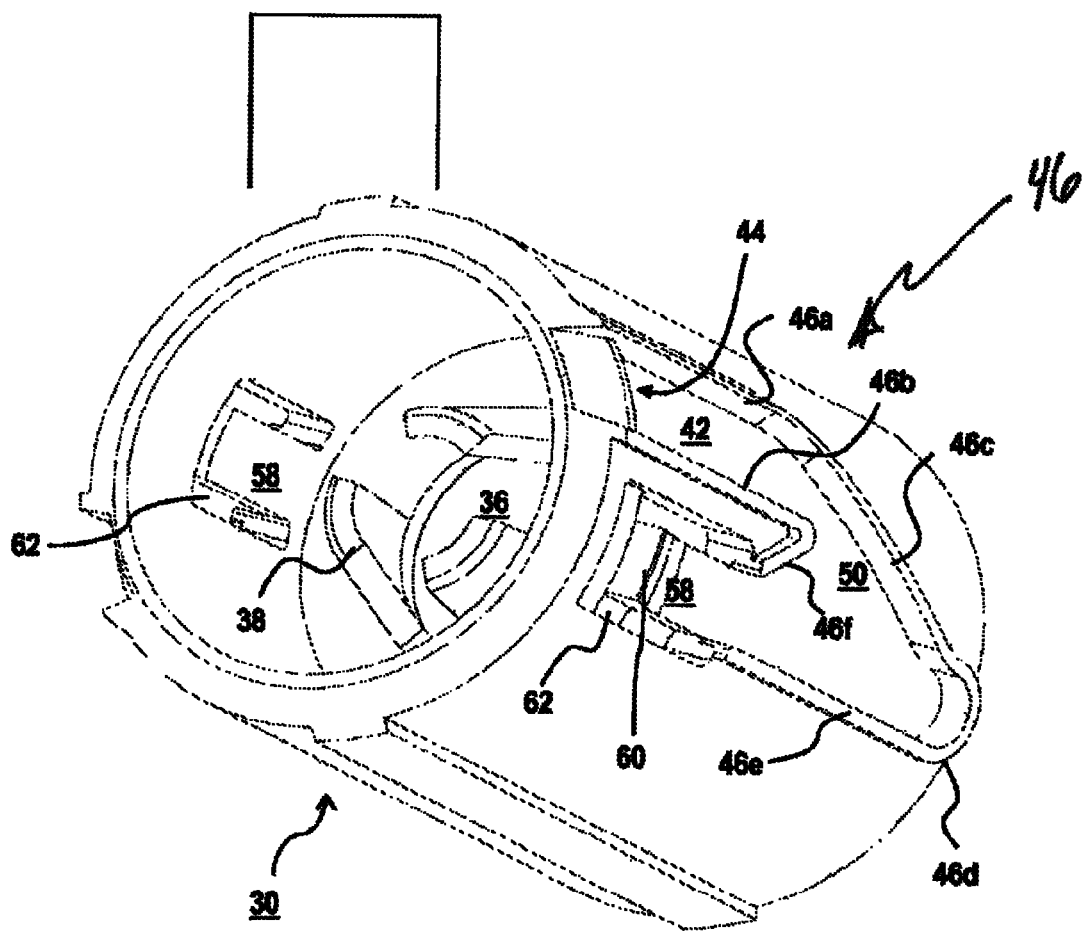
FIG. 2 shows a detailed perspective view of a rotatable sleeve comprised in the present invention.

In the first exemplary embodiment as shown in FIGS. 1 and 2, the generally tubular rotating sleeve, hereafter named rotator 30, comprises an inner diameter at its distal end. Said inner diameter is somewhat larger than the diameter of the proximal part of the hub such that the rotator surrounds the proximal part of hub, where a distal end surface 32 of the rotator 30 is in contact with the ledge 12 of the hub or arranged adjacent the ledge. The rotator is further arranged with an annular wall 34 extending transversally in relation to the longitudinal direction 18 of the device. The annular wall 34 is further provided with a central passage 36, which passage is provided with a number of flexible tongues 38 pointing in the proximal direction with some inclination such that when the rotator is connected to the hub, the tongues are in contact with the circumferential surface 24 of the needle attachment member 20 on the distal side of the conical shape 22, which thereby enables a rotating movement between the rotator 30 and the hub 10 but preventing a linear movement in the longitudinal direction. The distal surface of the annular wall 34 is provided with spacers 40, reducing the friction between the rotator and the hub.

Figure 6:
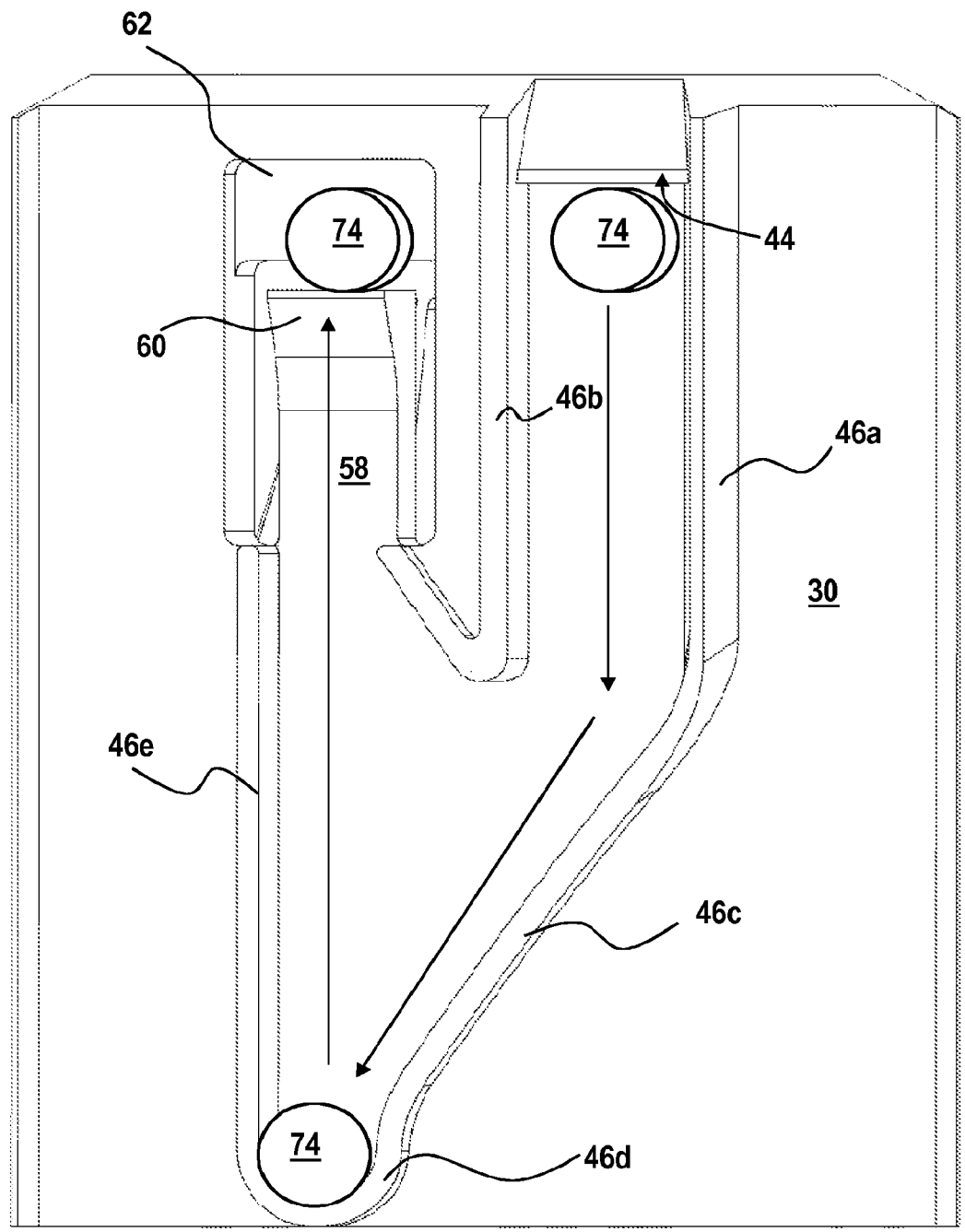
FIG. 6 shows a detailed view of a at least one first guide and locking means co-acting with at least one second guide and locking means.

In the first exemplary embodiment as shown in FIG. 6, the rotator comprises on its outer circumferential surface the at least one guide track 46. In the first exemplary embodiment the flexible means comprises the first flexible tongue 58 on the at least one guide track 46. The first flexible tongue 58 comprises a wedge-shaped outwardly directed protrusion, hereafter called the wedge 60, where the function thereof will be described below. As seen in FIGS. 2 and 6, the at least one guide track 46 comprises a first longitudinal section 42 limited by two parallel ledges 46a and 46b of the guide tracks as well as a transversal surface 44 arranged at the proximal end of the first section. The ledge 46a emerges into an inclined ledge 46c ending in a semi-circular ledge 46d forming the inclined section 50. The semi-circular ledge 46d continues thereafter in a straight ledge 46e directed in the longitudinal direction and the left ledge 46b of the first longitudinal section emerges into an inclined ledge 46f towards the proximal direction forming a second longitudinal section. At the proximal end of the two ledges 46e, 46f. Further, as seen in FIG. 6, adjacent the proximal end of the first flexible tongue the recess 62 has been made on the guide track. The corresponding structure is made on the opposite side of the rotator.

Figure 3:
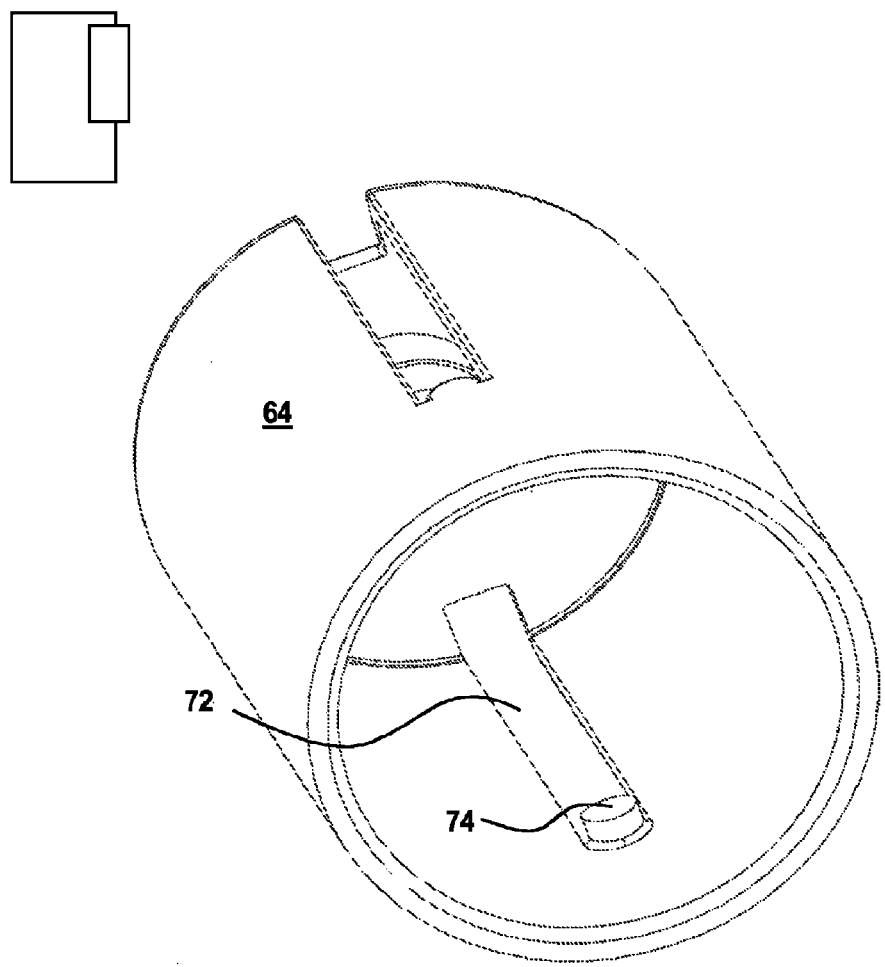
FIG. 3 shows a detailed perspective view of a needle shield comprised in the present invention.
Figure 4:
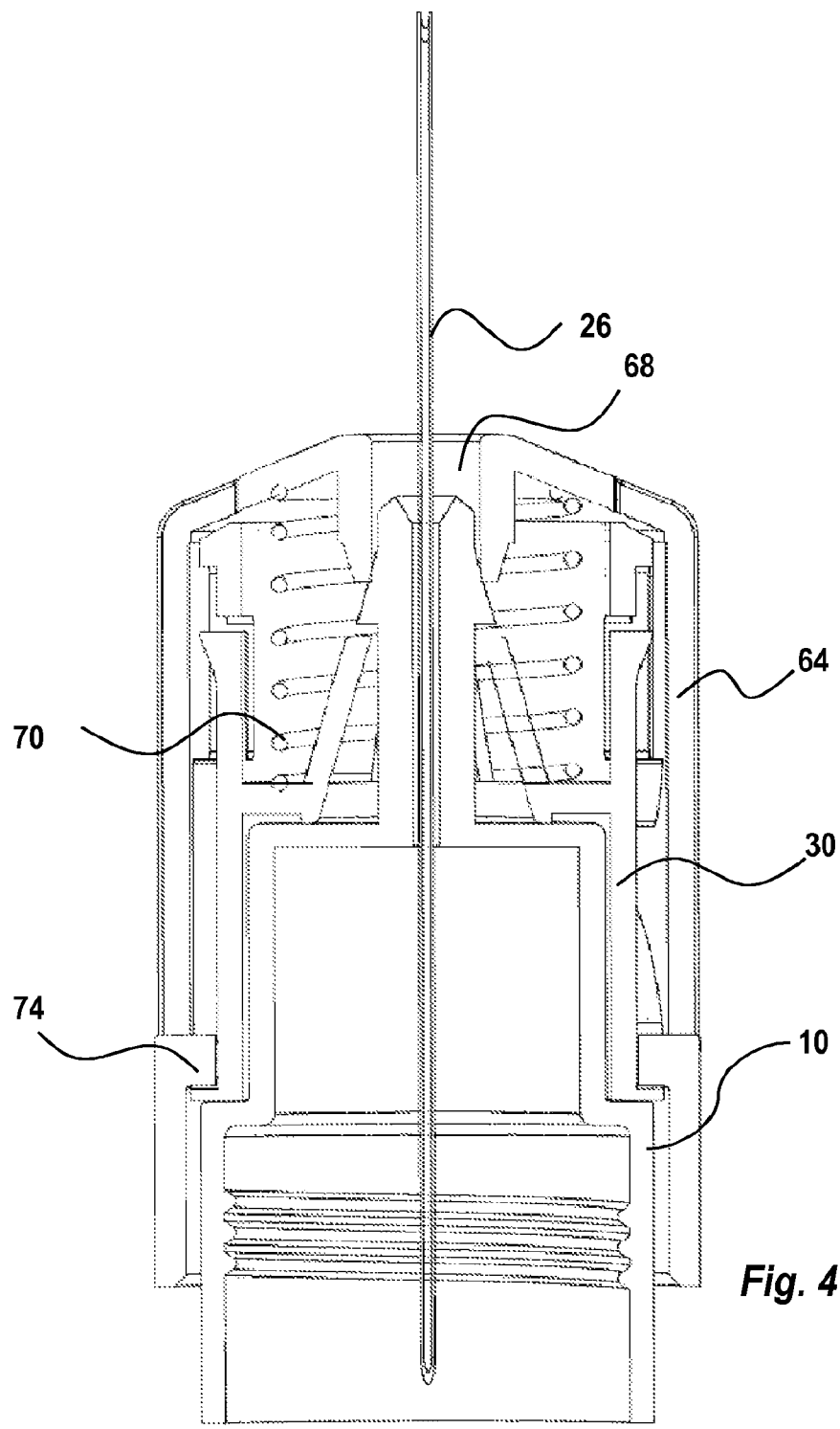
FIG. 4 shows a cross-sectional side view of the device of FIG. 1 when in an injection position.
Figure 5:
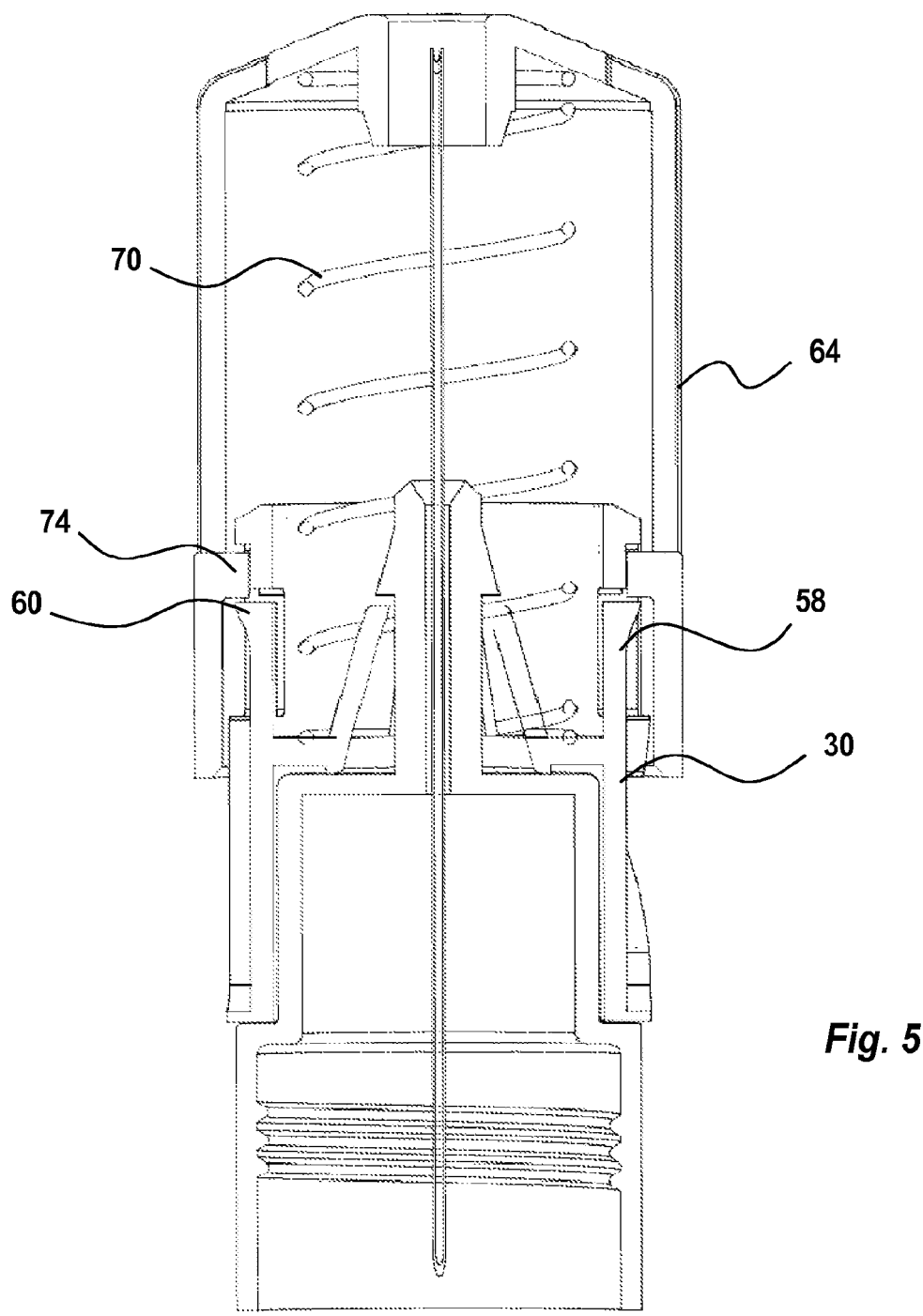
FIG. 5 shows a cross-sectional view of the device of FIG. 1 after completed injection and withdrawal from injection site.

In the first exemplary embodiment as shown in FIG. 3, the generally tubular needle shield 64 comprises a generally tubular part having a diameter somewhat larger than the outer diameter of the rotator 30 such that the needle shield surrounds the rotator.

In the first exemplary embodiment shown in the FIGS. 1, 3-5, and 6, the proximal end of the needle shield 64 is arranged with the end wall 66, which end wall is provided with the central opening 68 through which the injection end 28 of the injection needle 26 may pass, but said needle shield may also be provided without said wall 66. The needle shield 64 is arranged with two elongated slits 72, positioned opposite each other and extending in the longitudinal direction. These slits 72 are intended to cooperate with a cap (not shown) that is used when the safety pen needle device is attached to a medicament container. On the inner circumferential surface of the needle shield, at the distal end of the slits 72, at least one guide protrusion 74 is attached, or made integral with, the needle shield 64. These at least one guide protrusion 74 is intended to cooperate with the guide tracks 46 of the rotator 30 in a manner that will be described below.

In the first exemplary embodiment as shown in FIG. 6, the inclined section 50 is designed in such a form that when the needle shield 64 is displaced from the initial position to the injection position, the rotatable sleeve 30 is forced to rotate on the hub 10.

In the first exemplary embodiment as shown in FIG. 1, the resilient means such as a compression spring 70 is arranged between the annular wall 34 of the rotator 30 and the inner surface of the end wall 66 of the needle shield 64.

The safety pen needle device of the first exemplary embodiment is intended to function as follows. When the safety pen needle device is delivered to the user, a cap (not shown) having a closed proximal end, an open distal end and inwardly protruding means that cooperates with the slits 72 of the needle shield, is surrounding the safety pen needle device. The open distal end is sealed by a sealing means, such as a metal foil or plastic film or the like, for avoiding contamination of the non injection end of the injection needle. The sealing means are removed, and the hub is of the safety pen needle device is attached directly to a medicament container positioned in an injector or indirectly through a container holder such that the non-injection end 35 of the needle penetrates a septum of the medicament container. In this respect it is to be understood that the attachment means could be other than threads, such as for example bayonet fittings, snap-on mechanisms and the like. The needle shield is protected of movement by the cap. The cap is removed after the safety pen needle device is attached to the container and the proximal pointed injection end 28 of the needle is protected by the needle shield 64, i.e. the needle shield is in the initial position. The needle shield 64 is urged in the proximal direction by the spring 70 but stopped by the side surfaces of the guide protrusions 74 abutting the transversal surfaces 44.

A penetration and subsequent injection may now be performed. The proximal end of the safety pen needle device i.e. the proximal end of the needle shield is thus pressed against an injection site, i.e. the tissue of the patient. This causes the needle shield 64 to be coaxially and linearly moved on the rotator from the initial position to the injection position compressing the spring 70 for accumulating a force, whereby a penetration of the injection end of the needle into a tissue is performed, FIG. 4. During the penetration the guide protrusions 74 slide along the ledges of the guide tracks on the rotator through the first longitudinal section 42 and then through the inclined section 50. When the guide protrusions reach the inclined ledges 46c, they will cause the rotator 30 to rotate. Any rotation of the needle shield 64 is prevented due to the friction between the tissue of the patient and the proximal end of the needle shield.

After the injection is performed, the user withdraws the injector and thereby the safety pen needle device from the injection site. This causes the needle shield 64 to be pushed in the proximal direction by the accumulated force in the spring 70 in relation to the rotator 30, FIGS. 5, 6. This in turn causes the guide protrusions 74 of the needle shield 64 to move in the longitudinal direction along the ledges 46e until the guide protrusions come in contact with and move over the wedges 60 of the first flexible tongues 58, causing them to flex radial inwards, thereby permitting the passing of the guide protrusions 74, FIG. 6, which then fit into the recesses 62. The needle shield 64 is thus locked from coaxial and linear movement on the rotator due to the side surfaces of the recesses 62 and the transversal proximally facing surface of the wedges 60 of the first flexible tongues 58. The safety pen needle device may now be removed from the injector and discarded.

An exemplary second embodiment of the present invention is shown in the FIGS. 7 to 12. The generally tubular hub 80 comprises a proximal and a distal end. An inner circumferential surface of the hub 80 at the distal end thereof is arranged with attachment means such as threads 82, which are arranged to cooperate with corresponding attachment means such as threads of a medicament container (not shown) or of a container holder (not shown). An annular wall 84 is arranged inside said hub extending generally transversal to the longitudinal direction 86 of the device. The needle attachment member 88 is arranged to, or made integral with, said annular wall 84, where the needle attachment member 88 has a generally conical shape, narrowing towards the proximal end. In the centre of the needle attachment member the hollow injection needle 90 is attached. The injection needle 90 is provided with the proximal pointed injection end 92 and the distal pointed non-injection end 94, where the latter is arranged to penetrate a septum of the medicament container in order to provide a passage from the container through the needle 90 to the proximal injection end 92.

Figure 7:
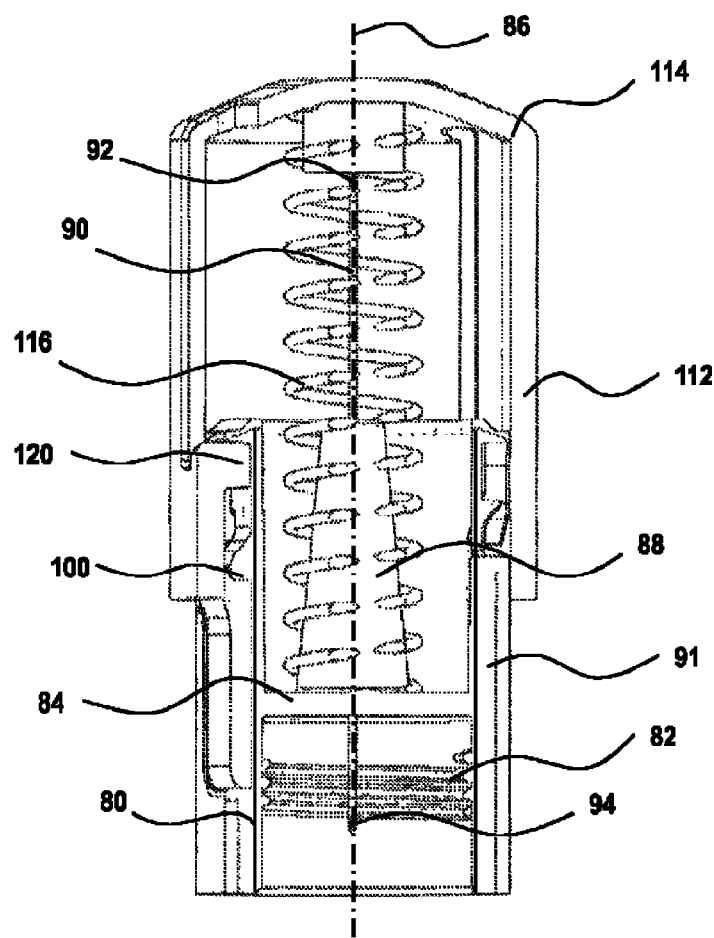
FIG. 7 shows a cross-sectional view of an alternative embodiment of the present invention in an initial state.
Figure 8:
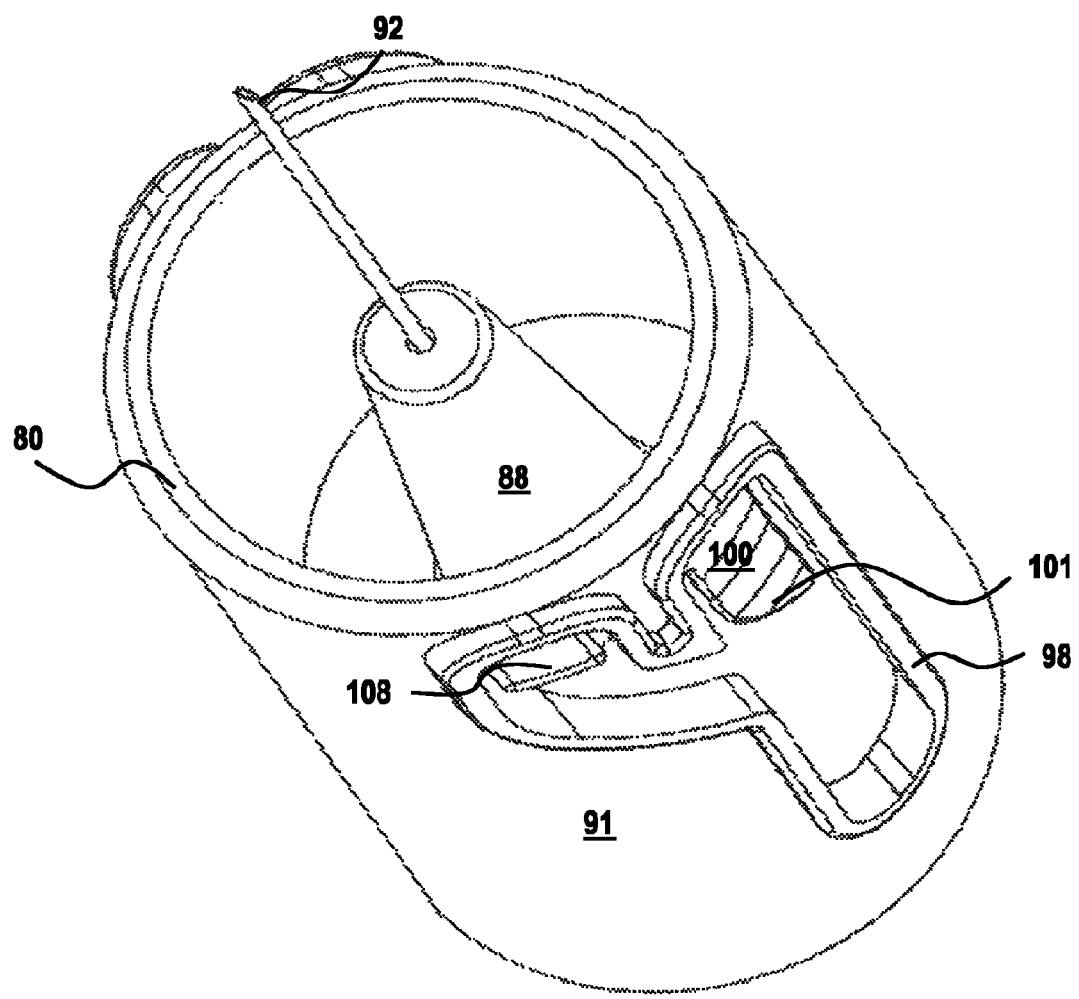
FIG. 8 shows a detailed view in perspective of a hub and a rotatable sleeve of the embodiment of FIG. 7.
Figure 10:
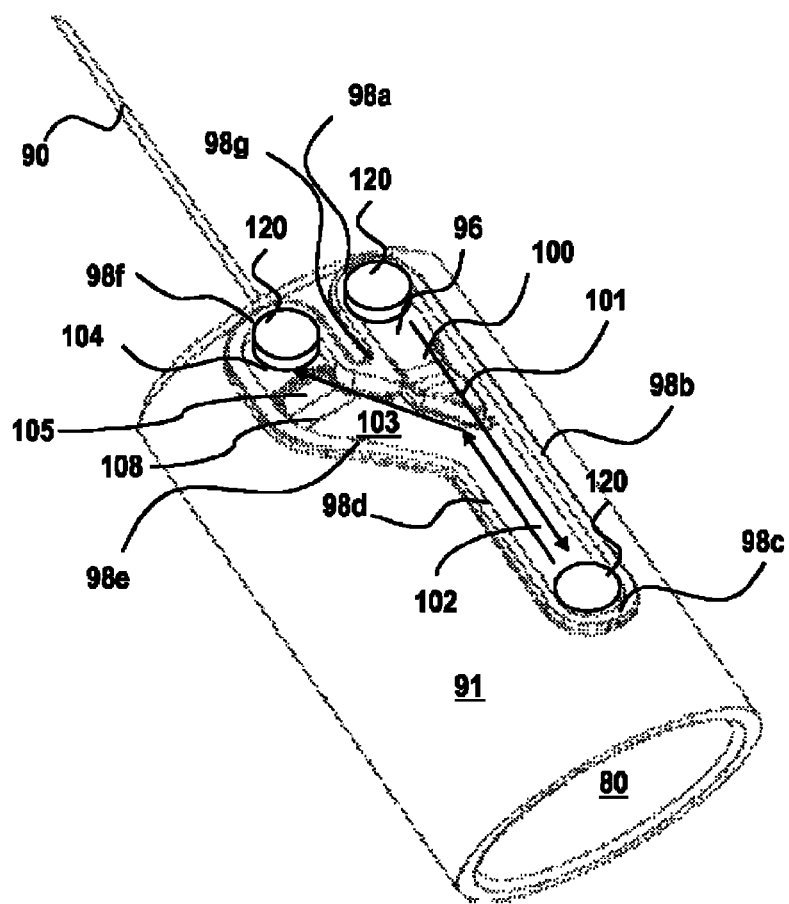
FIG. 10 shows a detailed view of a first guide and locking means co-acting with a second guide and locking means of the embodiment of FIG. 7.

In the second exemplary embodiment as shown in FIGS. 7 and 8, the generally tubular rotating sleeve, hereafter named rotator 91 is surrounding and rotatable connected to the hub. In contrast to the previous first exemplary embodiment, the rotator has in this second exemplary embodiment generally the same length as the hub, thus shortening the whole safety pen needle device. The outer circumferential surface of the rotator 91 is arranged with at least one guide track 98. In the second exemplary embodiment the flexible means comprises the first 108 and a second 100 flexible tongues. The first flexible tongue 108 comprises a wedge-shaped outwardly directed protrusion, hereafter called the first wedge 105, where the function thereof will be described below. As seen in FIG. 10 the at least one guide track 98 comprises a first longitudinal section 96, a second longitudinal section 102, the inclined section 103 and a fourth longitudinal section. The first longitudinal section is formed by a first semi-circular ledge 98a and by a straight ledge 98b arranged in the longitudinal direction of the rotator. The second flexible tongue 100 is provided on the guide track adjacent the first longitudinal section 96 and is arranged with a wedge-like outwardly directed protrusion, hereafter called the second wedge 101. The second section 102 is formed by the straight ledge 98b, by a second semi-circular ledge 98c which emerges from the straight ledge 98b and by a straight ledge 98d which emerges from the second semi-circular ledge 98c and extends towards the proximal end of the device. The inclined section 103 is formed by an inclined ledge 98e which emerges from the straight ledge 98d and by the wedge-like outwardly directed protrusion 101. The first flexible tongue 108 is arranged adjacent the fourth longitudinal section seen in the distal direction of the device and the fourth longitudinal section is formed by the recess 104 arranged between the boundaries of a third semi-circular ledge 98f which emerges from the inclined ledge 98e and the boundaries of the first flexible tongue 108. Lastly, the fourth longitudinal section is connected to the first longitudinal section 96 by a ledge 98g having an inclination corresponding to the ledge 98e. The corresponding structure is made on the opposite side of the rotator.

Figure 9:
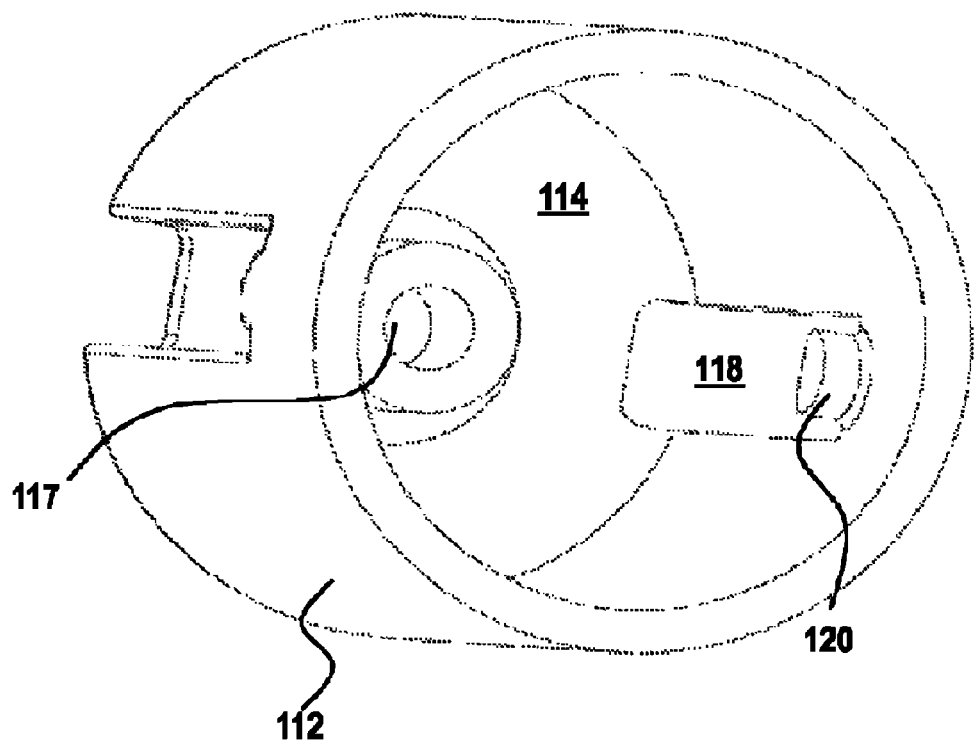
FIG. 9 shows a detailed view in perspective of a needle shield of the embodiment of FIG. 7.

In the second exemplary embodiment as shown in FIGS. 7 and 9, the generally tubular needle shield 112 has a diameter somewhat larger than the outer diameter of the rotator 91. Further, in the second exemplary embodiment as shown in FIGS. 7, 9, 11 and 12, the proximal end of the needle shield 112 is arranged with the end wall 114, which end wall is provided with the central opening 117 through which the injection end 92 of the injection needle 90 may pass, but said needle shield may also be provided without said wall 114. The needle shield 112 is arranged with two elongated slits 118, positioned opposite each other and extending in the longitudinal direction. These slits 118 are intended to cooperate with a cap (not shown) that is used when the safety pen needle device is attached to a medicament container. On the inner circumferential surface of the needle shield, at the distal end of the slits 118, the at least one guide protrusions 120 are attached, or made integral with, the needle shield. These guide protrusions 120 are intended to cooperate with the at least one guide track 98 of the rotator 91 in a manner that will be described below.

In the second exemplary embodiment as shown in FIG. 10, the inclined section 103 is designed in such a form that when the needle shield 112 is displaced from the injection position to the initial position, the rotatable sleeve 91 is forced to rotate on the hub 80.

Figure 11:
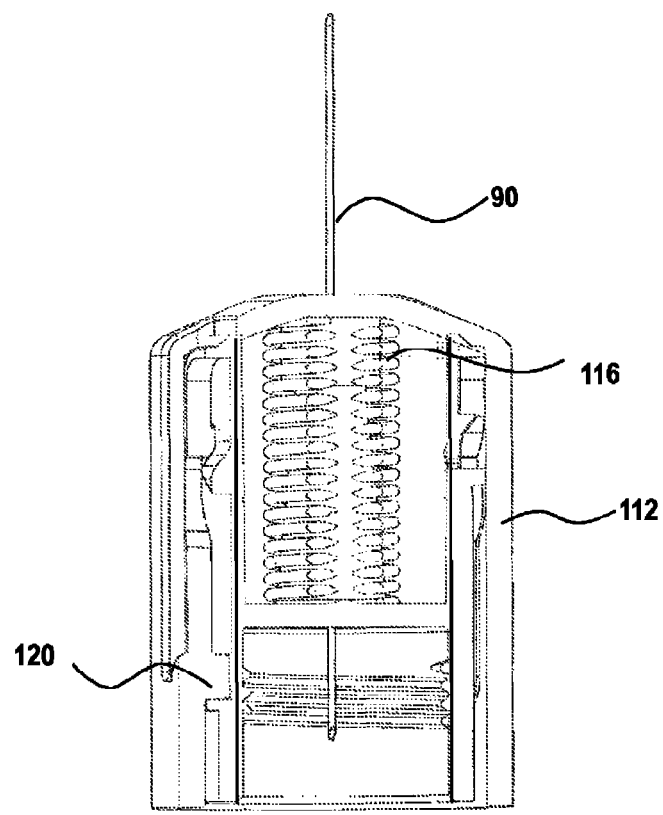
FIG. 11 shows a cross-sectional view of the embodiment of FIG. 7 when a penetration has occurred.
Figure 12:
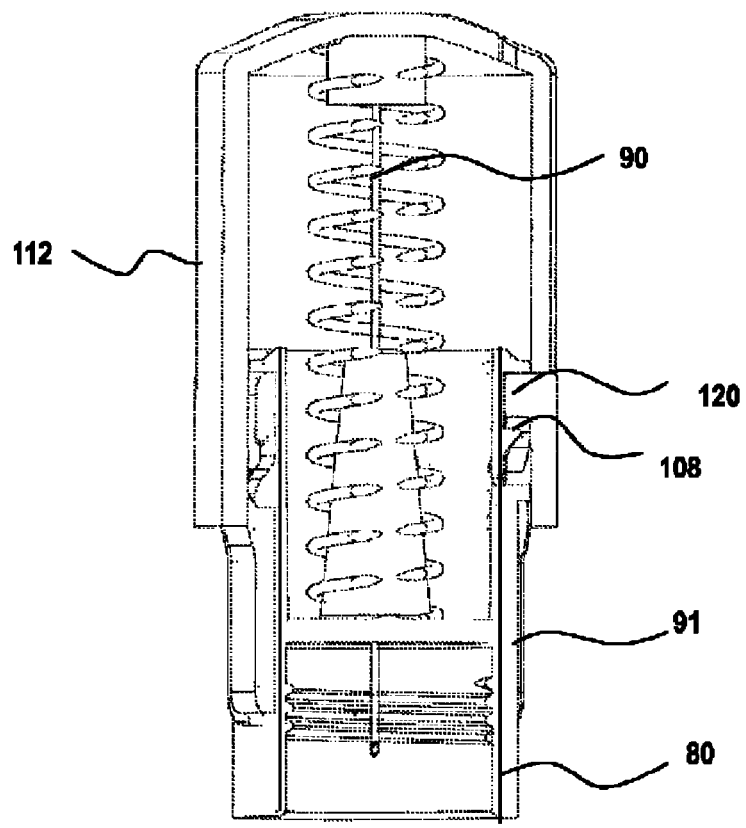
FIG. 12 shows a cross-sectional view of the device of FIG. 7 after completed injection and withdrawal from injection site.

In the second exemplary embodiment as shown in FIGS. 7, 11 and 12, the resilient means 116 such as a compression spring is arranged between the annular wall 84 of the hub 80 and the inner surface of the end wall 114 of the needle shield 112.

The safety pen needle device of the second exemplary embodiment is intended to function as follows. When the safety pen needle device is delivered to the user, a cap (not shown) having a closed proximal end, an open distal end and inwardly protruding means that cooperates with the slits 118 of the needle shield, is surrounding the safety pen needle device. The open distal end is sealed by a sealing means, such as a metal foil or plastic film or the like, for avoiding contamination of the non injection end of the injection needle. The sealing means are removed, and the hub is of the safety pen needle device is attached directly to a medicament container positioned in an injector or indirectly through a container holder such that the non-injection end 94 of the needle penetrates a septum of the medicament container. In this respect it is to be understood that the attachment means could be other than threads, such as for example bayonet fittings, snap-on mechanisms and the like. The needle shield is protected of movement by the cap. The cap is removed after the safety pen needle device is attached to the container and the proximal pointed injection end 92 of the needle is protected by the needle shield 112, i.e. the needle shield is in the initial position. The needle shield 112 is urged in the proximal direction by the spring 116 but stopped by the side surfaces of the guide protrusions 120 abutting the semi-circular ledge 98a of the first section 96 of the rotator 91.

A penetration and subsequent injection may now be performed. The proximal end of the safety pen needle device i.e. the proximal end of the needle shield is thus pressed against an injection site, i.e. the tissue of the patient. This causes the needle shield 112 to be coaxially and linearly moved on the rotator from the initial position to the injection position in which said needle shield is pushed in the distal direction compressing the spring 116 for accumulating a force, whereby a penetration of the injection end of the needle into a tissue is performed, FIG. 11. During the penetration the guide protrusions 120 slide along the first sections 96 of the guide tracks on the rotator passing the second wedges 101 of the second flexible tongues 100, by pressing the second flexible tongues 100 radial inwards, and then into the second section 102. After the guide protrusions 120 have passed over the second wedges 101, the second flexible tongues 100 are moved back radial outwards.

After the injection is performed, the user withdraws the injector and thereby the safety pen needle device from the injection site. This causes the needle shield 112 to be pushed towards the proximal direction of the device from the injection position to the initial position by the accumulated force in spring 116. This in turn causes the guide protrusions 120 of the needle shield 112 to move in the longitudinal direction along the ledge 98*d* until the guide protrusions 120 come in contact with a side wall of the second wedge 101. The side wall of the second wedge 101 has an inclination corresponding to the inclined ledge parts 98*e* and 98*g*, thereby forcing the guide protrusions 120 in that direction. This in turn causes the rotator 91 to turn or rotate in relation to the hub. Finally the guide protrusions move over the first flexible tongues 108, causing them to flex radial inwards, thereby permitting the passing of the guide protrusions 120, FIGS. 10 and 12, where the guide protrusions are prevented from further longitudinal movement by the third semi-circular ledges 98*f* and a side wall of the first wedges 105 of the first flexible tongues 108. The needle shield 112 is thus locked from longitudinal movement. The safety pen needle device may now be removed from the injector and discarded.

It is considered that instead of an end wall 66 or 114, the proximal end of the needle shield may be completely open. The resilient means 70 or 116 will then be arranged to act on an appropriate annular ledge on the distal part of the needle shield. It is also conceivable to have initial locking means that lock the needle shield to the hub before the safety pen needle device is used. The initial locking means may comprise a bayonet fitting such that the user twists the needle shield a certain angle in relation to the hub until the needle shield is free to be pushed into the hub during penetration as described above.

As a further development of the invention, the needle shield may comprises at least one window on its circumferential surface and the rotator may comprise visual indicia as e.g. colour, numbers, or the like on its outer surface that are visible on the at least one window. In this manner the user is provided with a visual indication that the safety pen needle device is used or not. Further the indicia may also be provide with at least one resilient arm having outwardly an directed protrusion of such a size that it may protrudes through the at least one window and outside the side surface of the needle shield such that they provide also tactile information that the safety pen needle device has been used. In this aspect the at least one resilient flexible arm also may provide audio information, such as a click sound, when they move into the openings.

It is to be understood that the embodiments described above and shown in the drawings only are to be regarded as non-limiting examples of the invention and that it may be modified in many ways within the scope of the patent claims.

The invention claimed is:

1. A safety needle device, comprising:
   a needle hub comprising:
      a proximal end,
      a distal end,
      an attachment mechanism arranged at the distal end for attaching the safety needle device to a medicament container, and
      a coaxially arranged needle attachment member;
   an injection needle comprising:
      a proximal pointed injection end, and
      a distal pointed non-injection end arranged to penetrate a septum of the medicament container,
      the injection needle being attached inside the needle hub and extending through the needle attachment member;
   a rotator arranged to rotate on the hub, the rotator arranged with an annular wall provided with a central passage, such that the needle attachment member of the needle hub extends through the central passage of the rotator;
   a needle shield surrounding the rotator and slidably arranged with respect to the hub and the rotator; and
   a resilient mechanism positioned between the needle shield and the rotator, the resilient mechanism co-acting with the needle shield for urging the needle shield toward a proximal end of the safety needle device.

2. The safety needle device of claim 1, wherein when the needle shield is linearly displaced in a distal direction, the needle shield acts on the rotator and forces the rotator to rotate with respect to the needle hub.

3. The safety needle device of claim 2, wherein when the needle shield is linearly displaced in the distal direction, an inner surface of the needle shield acts on the rotator and forces the rotator to rotate with respect to the needle hub.

4. The safety needle device of claim 3, wherein when the needle shield is linearly displaced in the distal direction, the inner surface of the needle shield acts on an outer surface of the rotator and forces the rotator to rotate with respect to the needle hub.

5. The safety needle device of claim 4, wherein when the needle shield is linearly displaced in the distal direction, the inner surface of the needle shield acts on an outer circumferential surface of the rotator and forces the rotator to rotate with respect to the needle hub.

6. The safety needle device of claim 2, wherein the needle shield is prevented from rotating when the needle shield is linearly displaced in the distal direction.

7. The safety needle device of claim 1, wherein the needle shield includes an end wall comprising a central opening, the central opening configured for passing the injection end of the injection needle.

8. The safety needle of claim 1 wherein the resilient mechanism comprises a compression spring.

9. The safety needle device of claim 1, wherein the needle shield is arranged to be linearly displaced from an initial position, in which the needle shield surrounds the injection end of the injection needle, to an injection position, in which the injection end of the injection needle is exposed outside the needle shield after the needle shield has been displaced toward a distal end of the safety needle device by pressing the needle shield against an injection site.

10. The safety needle device of claim 9, wherein the resilient mechanism is arranged to be compressed for accumulating a force when the needle shield is displaced from the initial position to the injection position, such that when the safety needle device is removed from the injection site, the needle shield is displaced from the injection position to the initial position by the force.

11. The safety needle device of claim 1, wherein the resilient mechanism is arranged between an annular wall of the rotator and an inner surface of an end wall of the needle shield.

12. The safety needle device of claim 1, wherein the rotator comprises at least one of audible indicia, visual indicia, and tactile indicia arranged for providing an indication that the safety needle device has been used.

13. The safety needle device of claim 1 wherein the attachment mechanism arranged at the distal end for attaching the safety needle device to the medicament container comprises a thread.

14. The safety needle device of claim 1 wherein the coaxially arranged needle attachment member comprises a conical shaped attachment member.

15. The safety needle device of claim 1 wherein the rotator comprises a tubular rotating sleeve.

16. The safety needle device of claim 1 wherein a distal surface of the annular wall of the rotator comprises spacers that reduce friction between the rotator and the hub.

17. The safety needle device of claim 1 wherein the needle shield comprises a generally tubular part having a diameter that is larger than an outer diameter of the rotator.

18. The safety needle device of claim 1 wherein the rotator surrounds the proximal end of the hub.

19. The safety needle device of claim 1 wherein the needle shield surrounds the rotator.

* * * * *